United States Patent [19]

Sircar et al.

[11] 4,082,757

[45] Apr. 4, 1978

[54] AMIDES OF 4-HYDROXY-6H-THIENO[2,3-b]THIOPYRAN-5-CARBOXYLIC ACID-7,7-DIOXIDE

[75] Inventors: Jagadish C. Sircar, Dover; Stephen J. Kesten, Morris Plains; Harold Zinnes, Rockaway, all of N.J.

[73] Assignee: Warner-Lambert Company, Morris Plains, N.J.

[21] Appl. No.: 749,491

[22] Filed: Dec. 10, 1976

[51] Int. Cl.² .................................. C07D 495/04
[52] U.S. Cl. ...................... 260/294.8 C; 260/306.8 R; 260/307 H; 260/329 HS; 424/263; 424/275
[58] Field of Search .................. 260/329 HS, 294.8 C; 424/263, 275

[56] References Cited

U.S. PATENT DOCUMENTS

| | | | |
|---|---|---|---|
| 3,457,269 | 7/1969 | Kirchner | 260/295.5 B |
| 3,636,041 | 1/1972 | Schmidt et al. | 260/332.2 C |

*Primary Examiner*—Alan L. Rotman
*Attorney, Agent, or Firm*—Albert H. Graddis; Frank S. Chow; Anne M. Kelly

[57] ABSTRACT

This invention relates to novel amides of 4-hydroxy-6H-thieno[2,3-b]thiopyran-5-carboxylic acid-7,7-dioxide having the Formula I:

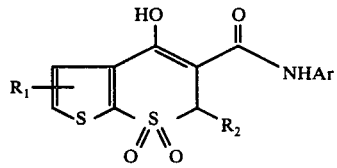

wherein $R_1$ is hydrogen, halogen or lower alkyl; $R_2$ is hydrogen, lower alkyl or aryl; Ar is aryl or heterocyclic; to the pharmaceutically acceptable salts thereof; and to processes for their preparation. The compounds of this invention exhibit antiinflammatory activity.

3 Claims, No Drawings

AMIDES OF 4-HYDROXY-6H-THIENO[2,3-b]THIOPYRAN-5-CARBOXYLIC ACID-7,7-DIOXIDE

DESCRIPTION OF THE INVENTION

This invention relates to novel amides of 4-hydroxy-6H-thieno[2,3-b]thiopyran-5-carboxylic acid-7,7-dioxide having the Formula I:

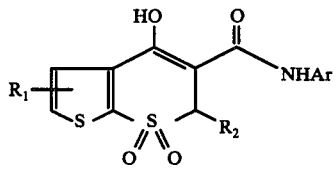

wherein $R_1$ is hydrogen, halogen or lower alkyl; $R_2$ is hydrogen, lower alkyl or aryl; Ar is aryl or heterocyclic and pharmaceutically acceptable salts thereof.

This invention also includes within its scope novel processes for preparing the above compounds as well as the intermediates employed in their synthesis.

Compounds of the Formula I are obtained by reacting a substituted 5,6-dihydro-4-oxo-4H-thieno[2,3-b]thiopyran-5-carboxylate of the Formula II:

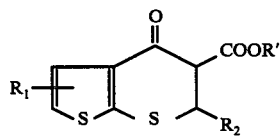

wherein $R_1$ and $R_2$ are as defined above in Formula I and R' is lower alkyl, in acetic acid with hydrogen peroxide to obtain a correspondingly substituted 4-hydroxy-6H-thieno[2,3-b]-thiopyran-5-carboxylate 7,7-dioxide of the Formula III:

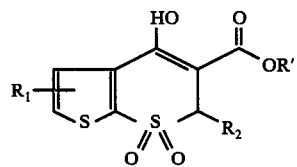

wherein $R_1$, $R_2$ and R' are as defined above in Formula II, which is heated with an appropriate amine in a suitable high boiling solvent, typically xylene, to obtain Compound I. Amines having the formula:

are suitable for use in this reaction, wherein Ar is a monocyclic aromatic hydrocarbon; a substituted monocyclic aromatic hydrocarbon wherein the substituent may be halogen, lower alkoxy, trifluoromethyl and the like; a monocyclic heterocycle; or a substituted monocyclic heterocycle wherein the substituent may be halogen, lower alkoxy, trifluoromethyl and the like. Typical amines include aniline, amino-substituted pyridine, amino-substituted isoxazole, amino-substituted thiazole and the like.

The starting material II is prepared as described in copending United States Application Ser. No. 749,507 filed Dec. 10, 1976, Jagadish C. Sircar, Stephen J. Kesten and Harold Zinnes, "5,6-Dihydro-4-Oxo-4H-Thieno[2,3-b]Thiopyran-5-Carboxamides" by refluxing a correspondingly substituted 5,6-dihydro-4H-thieno[2,3-b]thiopyran-4-one with a sodium alkoxide and a (dialkyl)oxalate in an appropriate solvent. According to this procedure, a 5,6-dihydro-4H-thieno[2,3-b]thiopyran-4-one (prepared as described in Bull. Soc. Chim. Fr. 2172 (1966) or chemically known, obvious variations thereof) is reacted with a sodium alkoxide, such as sodium methoxide and a (dialkyl)oxalate such as dimethyloxalate, in an appropriate solvent such as benzene to obtain an alkyl 4-hydroxy-α-oxo-6H-thieno[2,3-b]thiopyran-5-acetate, which is subjected to decarbonylation in the presence of powdered glass, at about 170° C. - 180° C. to obtain the desired alkyl 5,6-dihydro-4-oxo-4H-thieno-[2,3-b]thiopyran-5-carboxylate, II.

The compounds of this invention having Formula I exhibit antiinflammatory activity. When tested in a modification of the procedure described by Winter, et al., "Carrageenan Induced Edema in Hind Paw of the Rat for Anti-inflammatory Drugs", Proc. Exptl. Biol. and Med. 111: 544–547(1962). Thus, for example, when administered orally or intraperitoneally to rats at a dose of 6.25 to 100 mg/kg, they are able to cause reduction in swelling of the paw induced by an irritant such as carrageenin. 4-hydroxy-N-(2-pyridyl)-6H-thieno[2,3-b]-thiopyran-5-carboxamide 7,7-dioxide, when administered at a dose of 6.25mg/kg, demonstrates antiinflammatory activity in the rat in this test.

The compounds of this invention having Formula I are administered as aqueous suspensions or as aqueous solutions of their alkali metal salts.

The following definitions apply to all of the compounds, intermediates and processes of this invention: lower alkyl is meant to include 1 to 7 carbon, preferably 1 to 4 carbon, straight or branched alkyl chains; aforementioned definition of lower alkyl applies to the alkyl portion of the term lower alkoxy; halogen is meant to include chlorine, bromine and iodine; aryl is meant to include monocyclic aromatic hydrocarbons; substituted monocyclic aromatic hydrocarbons wherein the substituent may be halogen, lower alkoxy, trifluoromethyl and the like; monocyclic heterocycles; and substituted monocyclic heterocycles wherein the substituent may be halogen, lower alkoxy, trifluoromethyl and the like.

In order to further illustrate this invention, the following examples are provided:

EXAMPLE 1

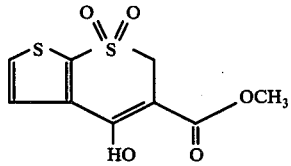

Methyl 4-hydroxy-6H-thieno[2,3-b]thiopyran-5-carboxylate 7,7-dioxide.

To a cooled (17°) suspension of methyl 5,6-dihydro-4-oxo-4H-thieno[2,3-b]thiopyran-5-carboxylate 7,7-dioxide To a cooled (17°) suspension of methyl 5-carboxylate (34.8 g, 0.1326 mole) in acetic acid (348 ml) is added dropwise 30% hydrogen peroxide (172.4 g, 1.526 mole). The mixture is stirred at room temperature for 2 hrs.

when a clear solution is formed. The solution is stirred at room temperature for an additional 4 hrs. It is then heated on a steambath for 12 min. to 94° C. and cooled immediately in an ice-bath. At around 18° C the product started to crystallize out. It is diluted with water (696 ml) and the mixture stirred at room temperature for 16 hrs. The solid ester is collected and recrystallized from methylene chloride-methanol mixture to give 12.3 g (31%) of white crystalline solid, m.p. 159°–162° C. An analytical pure sample, m.p. 159°–162° C. is obtained as white crystalline solid by further recrystallization from ethanol-methylene chloride. Yield 11.8 g (30%). IR (CHCl$_3$) 3140 (OH); 1660 (C=O); 1620 (C=C-C=O); 1160 (SO$_2$) cm$^{-1}$. NMR (CDCl$_3$) δ 12.7 (s, 1, OH, exchangeable); 7.5 (two d, 2, C$_2$,C$_3$); 4.3 (s, 2, C$_6$-H$_2$); 3.85 (s, 3, OCH$_3$). λ$_{max}$$^{EtOH}$ 320 (7,000), 240 (17,600) cm$^{-1}$.

Anal. Calcd. for C$_9$H$_8$O$_5$S$_2$: C, 41.53; H, 3.10; S, 24.64. Found: C, 41.58; H, 3.11; S, 24.59, 24.68.

EXAMPLE 2

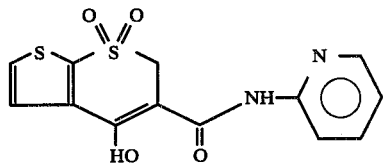

4-Hydroxy-N-(2-pyridyl)-6H-thieno[2,3-b]thiopyran-5-carboxamide 7,7-dioxide

A mixture of methyl 4-hydroxy-6H-thieno[2,3-b]thiopyran-5-carboxylate 7,7-dioxide (7.2 g; 0.028 mole), 2-aminopyridine (3.9 g; 0.042 mole) and xylene (720 ml) is refluxed for 2 hrs. in a Soxhlet apparatus, the thimble of which contains 20 g of Linde type 4A molecular sieve when a yellow solid crystallized out. The mixture is cooled to 5° in an ice-bath and the resulting crystalline precipitate is collected. It is recrystallized from THF to give 2.55 g of material, m.p. 194°–195° C. The xylene-filtrate is refluxed as before for an additional period of 3 hrs. It is concentrated to 300 ml, cooled and filtered to give a second crop, which is recrystallize from THF to give 1.5 g of the product, m.p. 193°–194° C. An analytical pure sample, m.p. 194°–195° C. is obtained as yellow crystalline solid by further recrystallization from DMF-ethanol mixture. IR (Nujol) 3160–3060 (broad, NH and OH); 1650 (C=O); 1620 (NH); 1150 (SO$_2$) cm$^{-1}$. NMR (DMSO) δ 10.8 (b, 1, NH); 8.5–7.1 (m, 6, aromatic), 4.6 (s, 2, CH$_2$). λ$_{max}$$^{EtOH}$ 368 (12,800), 265 (16,800), 242 (16,400) mμ

Anal. Calcd. for C$_{13}$H$_{10}$N$_2$O$_4$S$_2$: C, 48.44; H, 3.13; N, 8.69; S, 19.89. Found: C, 48.47; H, 3.30; N, 8.98; S, 19.77, 19.65.

EXAMPLE 3

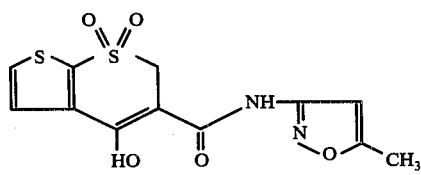

4-Hydroxy-N-(5-methyl-3-isoxazolyl)-6H-thieno[2,3-b]thiopyran-5-carboxyamide 7,7-dioxide.

A mixture of methyl 4-hydroxy-6H-thieno[2,3-b]thiopyran-5-carboxylate 7,7-dioxide (3.1 g, 0.012 mole), 3-amino-5-methylisoxazole (1.5 g, 0.015 mole) and xylene (120 ml) is refluxed for 1.5 hrs. in a Soxhlet apparatus, the thimble of which contains 15 g of Linde type 4A molecular sieve. The mixture is cooled to 5° C. in an ice-bath, and the resulting crystalline precipitate is collected. The filtrate is refluxed for two additional hours and then cooled to give a second crop. The two fractions are combined and recrystallized from CH$_2$Cl$_2$-CHCl$_3$ mixture to give a off-white crystalline solid (2.2 g, 56%), m.p. 209°–210° C. IR (Nujol) 3290–3100 (b, NH, OH); 1630 (C=O); 1570 (NH); 1150 (SO$_2$) cm$^{-1}$. NMR (DMSO) δ 11.2 (b, ~2, NH, OH, exchangeable); 8.1 (d, 1, C$_2$); 7.5 (d, 1, C$_3$); 8.63 (s, 1, C$_4$'), 4.5 (m, ~3, C$_5$,C$_5$); 2.4 (s, 3, C$_6$',CH$_3$). λ$_{max}$$^{EtOH}$ 350 (6,200); 254 (17,200) mμ

Anal. Calcd. for C$_{12}$H$_{10}$N$_2$O$_5$S$_2$: C, 44.17; H, 3.09; N, 8.58; S, 19.65. Found: C, 44.01; H, 3.09; N, 8.58; S, 19.45, 19.42.

EXAMPLE 4

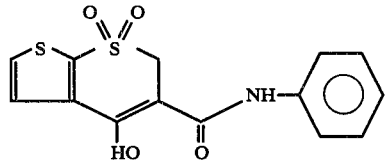

4-Hydroxy-N-phenyl-6H-thieno[2,3-b]thiopyran-5-carboxamide 7,7-dioxide

A mixture of methyl 4-hydroxy-6-H-thieno[2,3-b]thiopyran-5-carboxylate 7,7-dioxide (6.3 g, 0.024 mole), aniline (3 ml, 0.033 mole) and xylene (200 ml) is refluxed for 3 hrs. in a Soxhlet apparatus, the thimble of which contain 20 g of Linde 4A molecular sieve. The red solution is cooled to room temperature and the resulting crystalline precipitate is filtered, washed and dried. It is recrystallized from methylene chloride-ether mixture to give off-white solid (3.4 g), m.p. 133°–5° C. A second run of the reaction with the ester (3.2 g, 0.0123 mole), aniline (1.4 ml, 0.0154 mole) and xylene (100 ml) gives 2.8 g of the anilide. The products from the two runs are combined and recrystallized from methylene chloride-isopropyl ether to give 4.8 g of material, m.p. 136°–8° C. IR (CHCl$_3$) 3350 (b, OH, NH); 1695 (C=O); 1600 (NH); 1143 (SO$_2$) cm$^{-1}$. NMR (CDCl$_3$) δ 9.2 (b, 1, OH, NH); 7.5 (m, 7, aromatic); 4.3 (m, ~3, C$_5$, C$_6$). λ$_{max}$$^{EtOH}$ 340 (6,600), 252 (21,600) mμ

Anal. Calcd. for C$_{14}$H$_{11}$NO$_4$S$_2$: C, 52.32; H, 3.45; N, 4.36; S, 19.95. Found: C, 52.49; H, 3.62; N, 4.35; S, 19.53, 19.55.

EXAMPLE 5

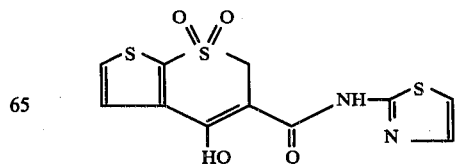

4-Hydroxy-N-(2-thiazolyl)-6H-thieno[2,3-b]thiopyran-5-carboxamide 7,7-dioxide A mixture of methyl 4-hydroxy-6H-thieno[2,3-b]thiopyran-5-carboxylate 7,7-dioxide (5.2 g, 0.02 mole), 2-aminothiazole (3.0 g, 0.03 mole) and xylene (175 ml) is warmed and filtered from the polymeric products. The filtrate is refluxed for 30 min. when some more polymeric product is formed. It is filtered again, and the filtrate refluxed for 1.5 hrs. The mixture is cooled to 5° C. in an ice-bath, and the resulting crystalline product is collected. It is dissolved in THF, treated with charcoal and filtered. The filtrate is concentrated to give the desired product (1.4 g, 21%), m.p. 215°–216° C. IR (Nujol) 3100 (broad, NH and OH); 1590 (CONH); 1155 (SO$_2$) cm$^{-1}$. NMR (DMSO) δ 11.0 (b, ~2, NH and OH); 8.1 (d, 1, C$_3$'); 7.5 (m, 2, C$_2$-C$_3$); 7.15 (d, 1, C$_4$'); 4.6 (s, 2, CH$_2$). $\lambda_{max}^{EtOH}$ 360 (14,600), 267 (12,400), 246 (11,600) mμ; mol. ion. 328.

Anal. Calcd. for C$_{11}$H$_8$N$_2$O$_4$S$_3$ (328): C, 40.23; H, 2.46; N, 8.53; S, 29.29. Found: C, 40.38; H, 2.65; N, 8.35; S, 28.32, 28.31.

We claim:

1. A compound of the Formula I:

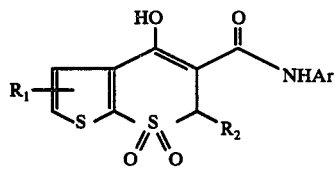

wherein R$_1$ is hydrogen, halogen or lower alkyl; R$_2$ is hydrogen, lower alkyl or phenyl; and Ar is phenyl or pyridyl; and its pharmaceutically acceptable salts.

2. A compound according to claim 1, which is 4-hydroxy-N-(2-pyridyl)-6H-thieno[2,3-b]thiopyran-5-carboxamide 7,7-dioxide.

3. A compound according to claim 1, which is 4-hydroxy-N-phenyl-6H-thieno[2,3-b]thiopyran-5-carboxamide 7,7-dioxide.

* * * * *